United States Patent [19]

Sawyer et al.

[11] Patent Number: 5,290,775
[45] Date of Patent: Mar. 1, 1994

[54] EUTHANASIA COMPOSITIONS

[75] Inventors: Donald C. Sawyer, Okemos; Marlee A. Langham, DeWitt; Theodore M. Brody, East Lansing, all of Mich.

[73] Assignee: Board of Trustees operating Michigan State University, East Lansing, Mich.

[21] Appl. No.: 709,193

[22] Filed: Jun. 3, 1991

Related U.S. Application Data

[63] Continuation-in-part of Ser. No. 631,090, Dec. 19, 1990.

[51] Int. Cl.$^5$ .................... A61K 31/54; A61K 31/44; A61K 31/47; A61K 31/16
[52] U.S. Cl. .................. 514/224.8; 514/289; 514/296; 514/313; 514/626; 514/629; 514/630
[58] Field of Search .................... 514/224.8, 289, 296, 514/313, 626, 629, 630

[56] References Cited

PUBLICATIONS

CA 86(4): 21733g, Federal Register, 41(201), 45547, Oct. 15, 1976.
Dialog Acc. No. 00050539, Drug Name: Chloroquine; Jaeger et al., Med-Toxicol 2/4 (242-273); 1991.
Tona et al., European Journal of Pharmacology, 178, 293-301 (1990).
Dialog Acc. No.: 01999557, American Hospital Formula Y Service; Monograph Title: Quinacrine Hydrochloride, 1991.
Mudge, Goodman and Gilman eds., pp. 866-874, 1985.
CA 106(7):43892s, Nath et al., 1986.
CA 103(21):171845d, Dallaire et al., 1985.
Don Michael et al., Am. Heart J., 79(6), 1970, pp. 831-842.
Mudge, G. H. and Weiner, I. M., Water, Salts and Ions. In Goodman and Gilman's The Pharmacological Basis of Therapeutics, Gilman, Rall, Nies and Taylor, Ed., New York, p. 846, Pergamon Press, Inc. (1990).

*Primary Examiner*—Frederick E. Waddell
*Assistant Examiner*—Kimberly R. Jordan
*Attorney, Agent, or Firm*—Ian C. McLeod

[57] ABSTRACT

An euthanasia solution based upon gamma-hydroxybutramide, a cardiotoxic amount of a compound selected from a chloroquine and quinacrine compound and lidocaine as a base or as a water soluble salt is described. The composition provides effective euthanasia without unwanted side effects, particularly in dogs, cats and horses. In addition, it does not contain substances controlled by the Federal Drug Control Administration.

29 Claims, No Drawings

EUTHANASIA COMPOSITIONS

CROSS-REFERENCE TO RELATED APPLICATION

This application is a continuation-in-part of U.S application Ser. No. 631,090, filed Dec. 19, 1990.

BACKGROUND OF THE INVENTION (1) Field of the Invention

The present invention relates to euthanasia compositions which are used for producing humane death in lower mammals. In particular the present invention relates to euthanasia solutions which contain the anesthetic gamma-hydroxybutramide (embutramide), a chloroquine or quinacrine compound and lidocaine or a salt thereof.

(2) Prior Art

Euthanasia compositions for lower mammals are necessary in order to provide humane death. Generally the solutions are injected intravenously or intraperitoneally. Users or user facilities of such solutions are animal control facilities, humane societies, veterinarians, veterinary hospitals, zoos and researchers. The owners of such animals are all concerned with providing humane death.

Euthanasia compositions containing barbiturates are on the market. These solutions are controlled by the U.S. Drug Enforcement Administration (DEA) because of the barbiturates which are Class II or Class III controlled substances. There is a need for compositions which are not controlled because of the record keeping involved in handling the barbiturate compositions.

The need to formulate a new euthanasia composition was prompted by problems with a euthanasia composition which was marketed under the name "T-61" and is no longer produced. It is comprised of an anesthetic, gamma-hydroxybutramide; a local anesthetic, tetracaine; a muscle relaxant, mebezonium; and a solvent, dimethylformamide. The composition of this solution contains as solids, 78% gamma-hydroxybutramide; 2% tetracaine (a local anesthetic); and 20% mebezonium, and as liquids a mixture of 60% dimethylformamide and 40% water. The solution contained 25.5% total solids and the solution has a non-viscous consistency and is injectable with a 22 gauge needle or larger.

A component of T-61 was causing adverse side effects when the product was rapidly injected intravenously. The physiological and pharmacological effects of each component of the euthanasia solution, T-61 were investigated. The anesthetic, gamma-hydroxybutramide, appeared to be an effective lethal drug at the recommended dose for T-61 (62 mg/kg). Its onset of action occurred within 15 to 25 seconds and has a smooth, calm induction with 47% ethanol used as an investigational vehicle. Mebezonium, the neuromuscular blocking agent included in T-61 was found to be effective at the concentration contained in T-61. The equi-effective dose of mebezonium is about 3 mg/kg and at the volume recommended for euthanasia with T-61, the dose of the muscle relaxant is 15 mg/kg IV. The onset of effect at the equi-effective dose is approximately 75 seconds.

Tetracaine hydrochloride (5 mg/ml; 1.5 mg/kg) appeared to be responsible for bizarre behavioral effects when T-61 was given rapidly. This dose is higher than those used for therapeutic purposes. This response, e.g., stiffening of the forelimbs, opisthotonos, and an apparent uneasy appearance was reproduced when tetracaine was given alone at the dose contained in T-61. This undesirable effect is most likely due to the direct stimulatory effects of tetracaine on the central nervous system. T-61 was recommended to be given slowly for this reason. In practice it was given rapidly and produced the undesired behavioral response. The euthanasia solutions approved by the FDA now for marketing do not allow a slow rate of injection since this is impractical in use.

Dimethylformamide (DMF) is the solvent used in T-61 to keep embutramide in solution. DMF is used at a 60% by volume in water concentration in T-61 and appears to have a local irritating effect at the site of injection. It also appears to have a central stimulating effect which is observed within the first 15 seconds following injection. This is then followed by a period of sedation lasting 15 to 30 minutes in some animals when given alone. It does not appear to alter the onset of anesthesia induced by embutramide nor contribute to the lethal effects of the anesthetic. DMF is most likely responsible for the discomfort induced when T-61 is given rapidly.

An additional problem with the T-61 composition is the appearance of a noticeable heart beat which persists during the euthanasia procedure. Although this activity of the heart is ineffective in perfusing body tissues, the heartbeat is nevertheless visible in thin chested dogs or small animals and usually persists for many minutes. This is not esthetically pleasing to the owner nor to people performing euthanasia.

Thus there is a need for an improved euthanasia solution. Gamma-hydroxybutramide is not included on the list of drugs controlled by the Federal Drug Enforcement Agency. In addition, it has a rapid onset of action causing almost immediate anesthesia and cessation of breathing. The problem then was to provide an effective formulation which overcomes the problems of the prior art with T-61.

The cardiac depressant and potential lethal effects of chloroquine and quinacrine are recognized. These drugs are used to treat malaria in human beings, but so far as is known, there has been no attempt to provide useful euthanasia formulations with these drugs.

In injectable formulations, the effects of high plasma concentrations of potassium on the heart is known. This can be seen in Mudge, G. H. and Weiner, I. M., Water, Salts and Ions. In Goodman and Gilman's *The Pharmacological Basis of Therapeutics*, Gilman, Rall, Nies and Taylor, Ed., New York, p 700, Pergamon Press, Inc. (1990).

In parent application Ser. No. 631,090, filed Dec. 19, 1990 gamma-hydroxybutramide and chloroquine or quinacrine compositions are described which are very effective in dogs. In cats the results were poor. Thus, there is a need for improved euthanasia compositions which are effective in cats, as well as other animals.

OBJECTS

It is therefore an object of the present invention to provide improved euthanasia compositions, which rapidly eliminate the presence of a noticeable heart beat and the stiffening encountered with T-61, and which are effective in cats as well as other animals. It is further an object to reduce or eliminate agonal breathing during the procedure. Another object of the present invention is to provide compositions which are relatively inexpensive and which do not contain DEA controlled substances. These and other objects will become increasingly apparent by reference to the following description.

GENERAL DESCRIPTION

The present invention relates to a method for providing euthanasia in a mammal which comprises: premedicating the mammal with a tranquilizer; and introducing into the mammal an aqueous solution comprising a cardiotoxic compound selected from the group consisting of a quinacrine compound and a chloroquine compound and a water solubilized gamma-hydroxybutramide in an anesthetic amount wherein euthanasia occurs in the mammal.

The present invention relates to a method for providing euthanasia in a mammal which comprises introducing into the mammal, an aqueous solution comprising an admixture of a cardiotoxic compound selected from the group consisting of a quinacrine compound or chloroquine compound in a cardiotoxic amount, a lidocaine selected from the group consisting of a water solubilized lidocaine as a base and water soluble salts thereof and a water solubilized gamma-hydroxybutramide in an anesthetic amount, wherein euthanasia occurs in the mammal.

Further, the present invention particularly relates to a method for providing euthanasia in a mammal which comprises introducing into the mammal an effective amount of a mixture of gamma-hydroxybutramide dissolved in a water miscible liquid solubilizing agent; a chloroquine compound, a lidocaine compound; and optionally a water soluble inorganic salt in an aqueous solution so that the mammal is euthanasized within five (5) minutes.

The present invention also relates to a composition for providing euthanasia in a mammal which comprises in admixture in an injectable aqueous solution a cardiotoxic compound selected from the group consisting of a quinacrine compound and a chloroquine compound; a lidocaine selected from the group consisting of lidocaine as a base and water soluble salts thereof and gamma-hydroxybutramide, wherein the solution contains a ratio of gamma-hydroxybutramide to chloroquine of between about 3 to 1 and 6 to 1 and a ratio of lidocaine to gamma-hydroxybutramide between about 0.01 and 0.015 to 1, preferably 0.012 and 0.014 to 1, and in an amount sufficient to produce euthanasia. A preferred ratio of lidocaine to gamma-hydroxybutramide is 1:7 to 1:8.

The present invention also relates to a composition for providing euthanasia in a mammal which comprises in admixture an aqueous solution, gamma-hydroxybutramide dissolved in a water immiscible liquid solubilizing agent; a water soluble chloroquine compound, a lidocaine compound; and a water soluble inorganic salt, wherein the solution contains a ratio of gamma-hydroxybutramide to chloroquine of between about 3 to 1 and 6 to 1 and a ratio of inorganic salt to gamma-hydroxybutramide of between about 0.01 to 0.02 and a ratio of lidocaine compound to gamma-hydroxybutramide of between about 0.01 and 0.015 to 1, preferably 0.012 and 0.014 to 1, and wherein the solution produces euthanasia.

The preferred compositions include as solids alone between about 70 to 80 percent by weight of the gamma-hydroxybutramide, 20 to 25 percent by weight of the chloroquine compound, 0.5 to 2.0% of the lidocaine compound, and between 0.8 and 2.0% by weight of the potassium salt. The composition preferably contains as liquids a mixture of about 40% by weight water and 60% by weight solvent, preferably ethanol or denatured alcohol in an amount sufficient to dissolve the solids. The solids are preferably between about 20 to 30 percent by weight of the solution. Within these ranges the lethal dosage of the composition as an aqueous solution injected into the animal is preferably between about 0.15 and 0.35 ml per kg of body weight. In general, if too little of the composition is given, the time to produce death is prolonged. If too much of the composition is given, unwanted side effects may be observed, such as agonal breathing.

The preferred pH of the solution is between about 4.5 and 7.2 and buffers can be used to provide a pH between 6 and 7. Buffers can include alkali metal bicarbonates, acetates, phosphates, as well as MOPS, HEPES, TRIS, and the like.

Preferably the potassium salt is potassium chloride. This salt has a known cardiotoxic activity as discussed above. Other salts are magnesium, manganese, cobalt and cadmium. Inorganic soluble salts also function to keep the other ingredients in solution.

The gamma-hydroxybutramide is preferably dissolved in a lower alcohol containing 1 to 3 carbon atoms. Most preferably ethanol, which appears to be the least irritating locally at the site of injection, is used. Denatured alcohol can also be used. Other solutions can be used as a solvent.

Lidocaine is 2-diethylamino-N-[2,6-dimethylphenyl] acetamide. The hydrochloride salt can be used and is commonly available. Lidocaine base can be solubilized in the solvent used for the gamma-hydroxybutramide.

The water used for the formulation should be free of contamination. The formulation is usually in injectable form.

In certain cases it may be desirable to package the solution in a form for multiple injection. The solution can be spray injected or injected vis a hypodermic needle.

In the preferred method between about 35 and 75 mg of gamma-hydroxybutramide, 5 and 20 mg of cardiotoxic compound, 0.2 to 1.0 mg of the lidocaine salt and preferably between about 0.5 and 3 mg of the water soluble potassium salt per kg of body weight of the mammal is used to produce death in the mammal. The composition is formulated so that it can be used at a dosage between about 0.15 and 0.35 ml per kg of body weight of the mammal for ease of administration.

It is necessary to solubilize the gamma-hydroxybutramide (and lidocaine base if used) into solution with ethanol or denatured alcohol and then combine it with the chloroquine compound previously dissolved in alcohol or water. Lidocaine base can be prepared in a 2% concentration (20 mg/ml) in alcohol (ethanol or denatured alcohol). Lidocaine hydrochloride is water soluble. The chloroquine compound is soluble in alcohol and the potassium salt is water soluble.

The dose of each component can be altered so that death occurs in 2.5 to 4 minutes instead of 1 to 2 minutes to reduce the incidence of agonal breathing as shown hereinafter.

It is accepted to use an analgesic combined with a tranquilizer in clinical animal patients prior to euthanasia. The tranquilizer and the analgesic will prevent agonal breathing. The preferred analgesic is butorphanol and the preferred tranquilizer is acepromazine. Other known analgesics, tranquilizers, and anesthetics can be used and are well known to those skilled in the art.

SPECIFIC DESCRIPTION

Preparation of Test Solutions

When embutramide and chloroquine stock solutions were mixed according to the "recipe" of Table 1, the final volume of both chloroquine and embutramide is greater than the amount of liquid added. For example, when 10 ml of alcohol is added to embutramide powder, the final volume after the dry chemical is dissolved in the alcohol is approximately 12.5 ml. Chloroquine diphosphate has a final volume of approximately 11.4 ml after being dissolved in 10 ml of water. Calculations are the actual mg/kg dosages based on the final volume of each component after dissolving in the stock solution.

In the initial studies used to determine the compositions of this formulation, exact uniformity of the mixtures was not as important as determining which compounds should be included. More conventional practice is to Q.S. to a larger volume such as 13 ml for embutramide and 12 ml for chloroquine.

TABLE 1

Stock solutions:
A: 3.5 or 4 gms embutramide in 10 ml of ethanol or denatured alcohol (stock)
B: 2 gms chloroquine in 10 ml of distilled water
C: 100 mg of potassium chloride in 5 ml of distilled water
   5 ml of sodium bicarbonate solution (75 mg/ml) = 10 ml total volume
D: 100 mg potassium chloride in 6.25 ml of distilled water
   + 3.75 ml of 2% lidocaine hydrochloride solution
E: 100 mg potassium chloride in 6.25 ml of distilled water
   + 3.75 ml of 2% lidocaine stock solution (200 mg powder 10 ml stock denatured alcohol)
F: 6.25 ml of distilled water + 3.75 ml of 2% lidocaine stock solution (200 mg powder + 10 ml stock denatured alcohol)

Mixture:
| | |
|---|---|
| 10 ml | stock solution A |
| 5 ml | stock solution B |
| 5 ml | stock solution C, D, E or F |
| 20 ml | total volume |

Table 2 shows the compositions of the formulations tested. Table 3 shows the final percentages of the final compositions tested.

TABLE 2

EMBUTRAMIDE
Dry wt: 3500 mg                    Final vol range: 12.6–12.7 ml
mg/ml in stock solution "A":       275.6–277.7 mg/ml
mg in 10 ml stock solution "A":    2756–2777 mg
mg/ml in mixed solution - 20 ml vol: 137.8–138.9 mg/ml
mg/kg based on vol dose:
0.25 ml/kg = 34.5 to 34.7 mg/kg
0.30 ml/kg = 41.3 to 41.7 mg/kg
0.35 ml/kg = 48.2 to 48.6 mg/kg
EMBUTRAMIDE
Dry wt: 4000 mg                    Final vol range: 13.1–13.3 ml
mg/ml in stock solution "A":       300.8–305.3 mg/ml
mg in 10 ml stock solution "A":    3008–3053 mg
mg/ml in mixed solution - 20 ml vol: 150.4–152.7 mg/ml
mg/kg based on vol dose:
0.25 ml/kg = 37.6 to 38.2 mg/kg
0.30 ml/kg = 45.1 to 45.8 mg/kg
0.35 ml/kg = 52.6 to 53.4 mg/kg
EMBUTRAMIDE
Dry wt: 5000 mg                    Final vol range: 14.2–14.4 ml

TABLE 2-continued mg/ml in stock solution "A":       347.2–352.1 mg/ml
mg in 10 ml stock solution "A":    3472–3521 mg
mg/ml in mixed solution - 20 ml vol: 173.6–176.1 mg/ml
mg/kg based on vol dose:
0.25 ml/kg = 43.4 to 44.0 mg/kg
0.30 ml/kg = 52.1 to 52.8 mg/kg
0.35 ml/kg = 60.8 to 61.6 mg/kg
EMBUTRAMIDE
Dry wt: 6000 mg                    Final vol range: 14.5–14.7 ml
mg/ml in stock solution "A":       408.2–413.8 mg/ml
mg in 10 ml stock solution "A":    4082–4138 mg
mg/ml in mixed solution - 20 ml vol: 204.1–206.9 mg/ml
mg/kg based on vol dose:
0.25 ml/kg = 51.0 to 51.7 mg/kg
0.30 ml/kg = 61.2 to 62.1 mg/kg
0.35 ml/kg = 71.4 to 72.40 mg/kg
CHLOROQUINE DIPHOSPHATE
Dry wt: 2000 mg                    Final vol range: 11.2–11.6 ml
mg/ml in stock solution "B":       172.4–178.6 mg/ml
mg in 5 ml stock solution "B":     862–893 mg
mg/ml in mixed solution - 20 ml vol: 43.1–44.7 mg/ml
mg/kg based on vol dose:
0.25 ml/kg = 10.8 to 11.2 mg/kg
0.30 ml/kg = 12.9 to 13.4 mg/kg
0.35 ml/kg = 15.1 to 15.6 mg/kg
CHLOROQUINE DIPHOSPHATE
Dry wt: 3000 mg                    Final vol range: 12.2–12.8 ml
mg/ml in stock solution "B":       234.4–245.9 mg/ml
mg in 5 ml stock solution "B":     1229.5 mg
mg/ml in mixed solution - 20 ml vol: 58.6–61.5 mg/ml
mg/kg based on vol dose:
0.25 ml/kg = 14.7 to 15.4 mg/kg
0.30 ml/kg = 17.6 to 18.5 mg/kg
0.35 ml/kg = 20.5 to 21.5 mg/kg
POTASSIUM CHLORIDE
Dry wt: 100 mg
mg/ml in stock solution "C":       10 mg/ml
mg in 5 ml stock solution "C":     50 mg
mg/ml in mixed solution - 20 ml vol: 2.5 mg/ml
mg/kg based on vol dose:
0.25 ml/kg = 0.625 mg/kg
0.30 ml/kg = 0.75 mg/kg
0.35 ml/kg = 0.875 mg/kg
SODIUM BICARBONATE
mg/ml of stock sodium bicarbonate solution: 75 mg/ml (75 mg × 5 ml = 375 mg added to solution "C")
mg in 5 ml of stock solution "C":  187.5 mg (375 mg/ 10 ml × 5 ml)
mg/ml in mixed solution - 20 ml vol: 9.4 mg
mg/kg based on vol dose:
0.25 ml/kg = 2.4 mg/kg
0.30 ml/kg = 2.8 mg/kg
0.35 ml/kg = 3.3 mg/kg
LIDOCAINE BASE
mg/ml of stock lidocaine (2% solution)*: 20 mg/ml (20 mg × 3.75 ml = 75 mg added to solution "C")
mg in 5 ml of stock solution "C":  37.5 mg (75 mg/ 10 ml × 5 ml)
mg/ml in mixed solution - 20 ml vol: 1.9 mg
mg/kg based on vol dose:
0.25 ml/kg = 0.47 mg/kg
0.30 ml/kg = 0.57 mg/kg
0.35 ml/kg = 0.66 mg/kg

*Stock lidocaine solution = 200 mg power + 10 ml denatured alcohol solution.

EMBUTRAMIDE STOCK SOLUTIONS

Several stock solutions of embutramide (stock solution "A") were prepared containing four different amount of embutramide ranging from 3500 to 6000 mg in each solution. This allowed one to alter the dose of embutramide administered without changing the volume injected into the animal. For example, at the lower embutramide concentrations, the administrations of the following volumes of final mixture yielded dose concentrations of embutramide as follows:

| 0.25 ml/kg = | approximately | 35 mg/kg body weight |
| 0.30 ml/kg = | | 42 mg/kg |
| 0.35 ml/kg = | | 49 mg/kg |

Similarly, the highest stock solution of embutramide yielded dose concentrations of embutramide after administration of the final mixture as follows:

| 0.25 ml/kg = | approximately | 51 mg/kg body weight |
| 0.30 ml/kg = | | 61 mg/kg |
| 0.35 ml/kg = | | 71 mg/kg |

CHLOROQUINE DIPHOSPHATE STOCK SOLUTIONS

In a similar manner, "low" and "high" chloroquine diphosphate stock solutions were prepared, yielding chloroquine diphosphate does concentrations following injection of the mixture as follows:

| "low" | | |
| 0.25 ml/kg = | approximately | 11 mg/kg body weight |
| 0.30 ml/kg = | | 13 mg/kg |
| 0.35 ml/kg = | | 15 mg/kg |
| "high" | | |
| 0.25 ml/kg = | approximately | 15 mg/kg body weight |
| 0.30 ml/kg = | | 18 mg/kg |
| 0.35 ml/kg = | | 21 mg/kg |

POTASSIUM STOCK SOLUTION

A potassium stock solution was prepared that yielded potassium does concentrations following injection of the final mixture as follows:

| 0.25 ml/kg = | approximately | 0.62 mg/kg body weight |
| 0.30 ml/kg = | | 0.75 mg/kg |
| 0.35 ml/kg = | | 0.87 mg/kg |

LIDOCAINE STOCK SOLUTION

Lidocaine base prepared in an alcohol solution to yield doses as follows:

| 0.25 ml/kg = | approximately | 0.5 mg/kg |
| 0.30 ml/kg = | | 0.6 mg/kg |
| 0.35 ml/kg = | | 0.7 mg/kg |

TABLE 3

| | 3.5 | % | 4.0 | % |
|---|---|---|---|---|
| Embutramide: | 2777 | = 74 | 3053 | = 76 |
| Chloroquine: | 893 | = 24 | 893 | = 22 |
| Potassium Chloride: | 50 | = 1 | 50 | = 1 |
| Sodium Bicarbonate: | — | | — | |
| Lidocaine: | 37.5 | = 1 | 37.5 | = 1 |

EXAMPLE 1

These tests focused on euthanasia solutions for use in cats. It was found that lidocaine HCl produced a smoother euthanasia in cats, without comprising the effects in dogs of the composition of Ser. No. 631,090. Previous studies also demonstrated that embutramide was the component in the solution responsible for injection reactions in cats. The more effective stock solution in dogs with lidocaine HCl added was 4 gm embutramide, 2 gm chloroquine, 100 mg KCl, and 100 mg of lidocaine HCl or in a denatured alcohol solution. However, this high dose of lidocaine HCl induced stimulatory effects in cats and it was thought that a lower dose was better, e.g., 75 mg at 0.25 ml/kg of the mixture. For these tests cats were premedicated with butorphanol (analgesic) and acepromazine (a tranquilizer) to avoid discomfort.

In an attempt to alleviate the injection reaction problem in cats, the concentration of embutramide was decreased to 3.5 gm in the stock solution. If the injection reaction was concentration dependent, then a lower concentration of embutramide might solve the problem while still being high enough to achieve euthanasia with a single dose.

Two solutions, using the lower concentration of embutramide, were selected for testing, one with lidocaine HCl and no NaHCO$_3$, and one with NaHCO$_3$ but no lidocaine HCl. Buffering lidocaine HCl with NaHCO$_3$ caused he solution to precipitate.

Three different IV techniques of IV injection were examined to further evaluate whether the observed undesirable responses were caused by the speed of injection and/or concentration of embutramide. We found that the responses were caused by the high embutramide concentrations.

Dogs were included as well to assure that any modifications that were found to be effective in cats would also be efficacious in dogs.

METHODS

Testing in dogs and cats followed the same protocol as described earlier. An IV catheter was placed in the cephalic vein of dogs and cats scheduled for euthanasia at the Ingham County Animal Control Facility, Mason, Mich. One-half of the animals were premedicated with butorphanol (B) (0.1 mg/kg) combined with acepromazine (A) (0.15 mg/kg) (B/A) IV 4 to 6 minutes prior to the injection of a test solution. Two stock solutions were evaluated (Table 3): one composed of 3.5 embutramide, chloroquine, potassium chloride and sodium bicarbonate (ECKB), the other composed of 3.5 embutramide, chloroquine, potassium chloride and lidocaine HCl (ECKL).

TABLE 3

STOCK SOLUTIONS

A. 3.5 grams embutramide in 10 ml of stock denatured alcohol
B. 2 grams chloroquine diphosphate in 10 ml of H$_2$O
C. 100 mg KCl in 5 ml of H$_2$O + 5 ml of NaHCO$_3$ (75 mg/ml)
D. 100 mg KCl in 6.25 ml H$_2$O + 3.75 ml of 2% lidocaine solution MIXTURES
1. A + .5 B + .5 C (designated as 3.5 ECKB)
2. A + .5 B + .5 D (designated as 3.5 ECKL)

These were administered in a randomized blinded format at a dose of 0.25 ml/kg for cats and 0.35 ml/kg for dogs. The person evaluating the response did not know the components of the test solutions. These doses were based on previous studies for each species. These two solutions were injected using 3 different techniques: 1) IV push—the entire volume of solution injected within 1 to 2 seconds, 2) IV slow—the volume of solution injected over 15 seconds, and 3) IV ½ dose bolus—one half of the solution injected IV push with the remaining ½ of the dose administered IV push 30 seconds after the first ½ of the dose.

DOGS

Each solution was tested in 30 dogs; 15 were premedicated with B/A as described above and 15 were unpremedicated. The group of fifteen dogs was further divided into 3 groups of five animals each in which the solutions were injected with three different methods as indicated above.

CATS

This same format was followed in cats except that each solution was administered to 36 cats; 18 of which were premedicated with B/A and 18 not premedicated. Each group of 18 cats was then divided into 3 groups of 6 cats each which was euthanized using one of the 3 different injection techniques.

Scoring criteria are listed in Table 4. If an animal demonstrated agonal breathing, as defined in Table 4, the score of 1 to 5 was designated with the addition of an "A". Animals needing more drug following the initial injection to complete the euthanasia were designated with a "M".

TABLE 4

SCORING*

1. Smooth induction, no reaction to the injection, death occurs within 3 minutes.
2. Smooth induction, no reaction to the injection, heart beat is visible more than 3 minutes but less than 5 minutes.
3. Animal shows a reaction to the injection; heart beat visible for less than 3 minutes.
4. Animal shows a reaction to the injection; heart beat is visible more than 3 minutes but less than 5 minutes.
5. Unsatisfactory euthanasia: bad reaction AND/OR animal does not die and must be given another drug or euthanasia after 5 minutes.

*Scores will be designated with an "A" if agonal breathing occurred. Agonal breathing is defined as any breath taken immediately before or after the heart beat is no longer visible.

For cats that showed a reaction to injection, e.g., those that received a 3, 4, or 5, they were further evaluated as follows: 1 if they looked at the injection site, 2 if they pulled the leg or moved, or 3 if they vocalized. These were additionally graded with an a for a mild behavioral reaction; b for a moderate reaction; or c for a strong reaction. If an animal vocalized in response to the injection, the score would be 3; the second letter score indicated the severity of the vocal response: a for a soft moan; b for a cry; or c for a louder response.

RESULTS

The results for dogs are summarized in Table 5.

TABLE 5

SCORES AND TIME OF DEATH - DOGS GIVEN EMBUTRAMIDE, CHLOROQUINE SALT, POTASSIUM CHLORIDE, BUFFERED WITH NaHCO₃ WITH AND WITHOUT PREMEDICATION

| Solution #1 | | | |
|---|---|---|---|
| 3.5 ECKB - no premed | | 3.5 ECKB - B/A premedication | |
| IV PUSH scores | time of death | IV PUSH scores | time of death |
| 1 | 1:00 (min:sec) | 5 MR | 5:00 (min:sec) |
| 1 | 3:00 | 3 | 1:15 |
| 1 | 1:30 | 1 | 1:40 |
| 1 A | 2:00 | 2 | 3:30 |
| 2 | 4:45 | 2 | 4:30 |
| 1.2 ± 0.2 | 2:27 ± 0:40 | 2.6 ± 0.7 | 3:11 ± 0:45 |
| IV SLOW scores | time of death | IV SLOW scores | time of death |
| 2 | 4:00 | 2 | 5:00 |
| 2 A | 5:00 | 2 | 4:45 |
| 1 A | 3:00 | 2 | 4:00 |
| 1 | 2:45 | 2 | 4:30 |
| 2 | 3:30 | 2 | 5:00 |
| 1.6 ± 0.3 | 3:39 ± 0:24 | 2.0 ± 0.0 | 4:39 ± 0:11 |
| ½ BOLUS scores | time of death | ½ BOLUS scores | time of death |
| 5 ARM | 5:00 | 2 | 4:00 |
| 2 | 4:00 | 1 | 3:00 |
| 5 M | 5:00 | 1 | 2:00 |
| 1 A | 2:45 | 2 | 4:00 |
| 4 | 3:30 | 2 | 5:00 |
| 3.4 ± 0.8 | 4:03 ± 0:26 | 1.6 ± 0.3 | 3:36 ± 0:31 |
| % AGONAL: 20 | | % AGONAL: 0 | |

*CODES: A - agonal breathing, R - reaction to injection, M - If time of death was greater than 5:00, more drug was given to complete euthanasia
Solution #1, 3.5 ECKB/no premed, had acceptable scores for either the IV push or IV slow but not for the ½ bolus.

Agonal breathing occurred in 30 per cent of the dogs with acceptable scores and the time of death was between 2:27 and 3:39 minutes. When dogs were premedicated with B/A and given this same solution, the scores were slightly higher, 2.6 vs 1.2 for IV push and 2.0 vs 1.6, respectively. The IV slow in which the solution is injected over a 15 second period scored best with the dogs premedicated. No agonal breathing was observed. The time of death in the premedicated group was more than 3 minutes. However, the IV push with no B/A still had the best score.

If the 3.5 ECKB is compared with the ECKL in dogs not premedicated (Table 6), the best score was still 3.5 ECKB injected by IV push. There was a 30 per cent incidence of 5 scores in the IV push and IV slow dogs with the lidocaine added compared to no 5 scores in the ECKB groups respectively and the mean time of death was longer, e.g., about 4 minutes.

TABLE 6

DOGS COMPARISON OF SOLUTIONS 1 AND 2 WITHOUT PREMEDICATION

| Solution #1 | | Solution #2 | |
|---|---|---|---|
| 3.5 ECKB - no premed | | 3.5 ECKL - no premed | |
| IV PUSH scores | time of death | IV PUSH scores | time of death |
| 1 | 1:00 | 5 M | 5:00 |
| 1 | 3:00 | 1 | 2:30 |
| 1 | 1:30 | 2 | 4:30 |
| 1 A | 2:00 | 3 | 2:50 |
| 2 | 4:45 | 2 A | 4:45 |
| 1.2 ± 0.2 | 2:27 ± 0:40 | 2.6 ± 0.7 | 3:55 ± 0:31 |
| IV SLOW | | IV SLOW | |

TABLE 6-continued

DOGS
COMPARISON OF SOLUTIONS 1 AND
2 WITHOUT PREMEDICATION

| scores | time of death | scores | time of death |
|---|---|---|---|
| 2 | 4:00 | 5 M | 5:00 |
| 2 A | 5:00 | 1 A | 2:45 |
| 1 A | 3:00 | 5 M | 5:00 |
| 1 | 2:45 | 1 A | 2:20 |
| 2 | 3:30 | 4 | 3:15 |
| 1.6 ± 0.3 | 3:39 ± 0:24 | 3.2 ± 0.9 | 3:40 ± 0:34 |
| ½ BOLUS scores | time of death | ½ BOLUS scores | time of death |
| 5 ARM | 5:00 | 2 | 3:45 |
| 2 | 4:00 | 2 | 4:30 |
| 5 M | 5:00 | 5 M | 5:00 |
| 1 A | 2:45 | 2 | 3:30 |
| 4 | 3:30 | 1 | 1:00 |
| 3.4 ± 0.8 | 4:03 ± 0:26 | 2.4 ± 0.8 | 3:33 ± 0:41 |

However, with the dogs premedicated (Table 7), the best scores were in the 3.5 ECKL group.

TABLE 7

COMPARISON OF ECKB and ECKL SOLUTIONS
(L = Lidocaine HCl)
WITH B/A PREMEDICATION GIVEN TO DOGS

| Solution #1 3.5 ECKB - B/A premed | | Solution #2 3.5 ECKL - B/A premed | |
|---|---|---|---|
| IV PUSH scores | time of death | IV PUSH scores | time of death |
| 5 MR | 5:00 | 1 | 1:00 |
| 3 | 1:15 | 1 | 2:30 |
| 1 | 1:40 | 1 | 2:45 |
| 2 | 3:30 | 1 | 1:00 |
| 2 | 4:30 | 1 | 3:00 |
| 2.6 ± 0.7 | 3:11 ± 0:45 | 1.0 ± 0.0 | 2:03 ± 0:26 |
| IV SLOW scores | time of death | IV SLOW scores | time of death |
| 2 | 5:00 | 3 | 2:00 |
| 2 | 4:45 | 2 | 4:00 |
| 2 | 4:00 | 1 | 3:00 |
| 2 | 4:30 | 2 | 3:30 |
| 2 | 5:00 | 1 | 3:00 |
| 2.0 ± 0.0 | 4:39 ± 0:11 | 1.8 ± 0.4 | 3:04 ± 0:20 |
| ½ BOLUS scores | time of death | ½ BOLUS scores | time of death |
| 2 | 4:00 | 1 | 2:00 |
| 1 | 3:00 | 2 | 4:00 |
| 1 | 2:00 | 2 | 3:15 |
| 2 | 4:00 | 2 | 3:15 |
| 2 | 5:00 | 2 | 4:00 |
| 1.6 ± 0.3 | 3:36 ± 0:31 | 1.8 ± 0.2 | 3:18 ± 0:22 |

The results for cats are summarized in Table 8.

TABLE 8

COMPARISON OF ECKB AND ECKL GIVEN TO CATS
WITH AND WITHOUT BUTORPHANOL AND
ACEPROMAZINE PRIOR TO EUTHANASIA

| Solution #1 | | | | | |
|---|---|---|---|---|---|
| 3.5 ECKB - no premed | | | 3.5 ECKB - B/A premed | | |
| IV PUSH score | rxn | time | IV PUSH score | rxn | time |
| 5 M | 3a | 5:00 | 2 | | 3:00 |
| 3 | 3c | 1:00 | 2 | | 4:55 |
| 5 | 3c | 1:30 | 3 | 1a* | 1:00 |
| 3 | 3b | 1:30 | 2 | | 4:00 |
| 3 | 3c | 2:15 | 1 | | 2:30 |
| 3 | 2c | 3:00 | 1 | | 2:45 |
| mean = 3.7 | | 2:22 | mean = 1.8 | | 3:00 |
| SEM = 0.4 | | 0:36 | SEM = 0.3 | | 0:32 |
| IV SLOW | | | IV SLOW | | |

TABLE 8-continued

COMPARISON OF ECKB AND ECKL GIVEN TO CATS
WITH AND WITHOUT BUTORPHANOL AND
ACEPROMAZINE PRIOR TO EUTHANASIA

| score | rxn | time | score | rxn | time |
|---|---|---|---|---|---|
| 5 M | 0 | 5:00 | 5 M | 0 | 5:00 |
| 3 | 3b | 3:00 | 2 | | 4:00 |
| 1 | | 2:00 | 5 M | 2a | 5:00 |
| 3 | 3a | 2:00 | 1 | | 2:00 |
| 5 M | 0 | 5:00 | 2 | | 4:30 |
| 2 | | 2:45 | 2 | | 4:00 |
| mean = 3.2 | | 3:17 | mean = 2.8 | | 4:05 |
| SEM = 0.7 | | | SEM = 0.7 | | 0:27 |
| ½ BOLUS score | rxn | time | ½ BOLUS score | rxn | time |
| 5 M | 1c | 5:00 | 5 M | 0 | 5:00 |
| 3 | 3c | 1:30 | 2 | | 5:00 |
| 3 | 2b | 2:45 | 4 | 3b | 5:00 |
| 2 | | 4:30 | 4 | 2b | 5:00 |
| 5 M | 3a | 5:00 | 3 | 3a | 2:00 |
| 5 M | 0 | 5:00 | 2 | | 4:45 |
| mean = 3.8 | | 3:58 | mean = 3.3 | | 4:28 |
| SEM = 0.5 | | 0:36 | SEM = 0.5 | | 0:30 |
| PERCENT REACTIONS: | | 66.7 | PERCENT REACTIONS: | | 27.7 |

| Solution #2 | | | | | |
|---|---|---|---|---|---|
| 3.5 ECKL - no premed | | | 3.5 ECKL - B/A premed | | |
| IV PUSH score | rxn | time | IV PUSH score | rxn | time |
| 5 M | 2a | 5:00 | 3 | 3c | 3:00 |
| 5 M | 2b | 5:00 | 5 M | 0 | 5:00 |
| 3 | 3c | 1:30 | 2 | | 4:00 |
| 1 A | | 2:30 | 2 | | 3:00 |
| 3 | 3c | 2:00 | 5 M | 0 | 5:00 |
| 1 | | 2:30 | 2 | | 4:00 |
| mean = 3.0 | | 3:05 | mean = 3.2 | | 4:00 |
| SEM = 0.7 | | 0:37 | SEM = 0.6 | | 0:22 |
| IV SLOW score | rxn | time | IV SLOW score | rxn | time |
| 1 | | 3:00 | 5 M | 0 | 5:00 |
| 3 | 1a | 1:30 | 5 M | 2a | 5:00 |
| 5 M | 2c | 5:00 | 5 M | 0 | 5:00 |
| 3 | 2a | 2:30 | 5 M | 0 | 5:00 |
| 5 M | 3c | 5:00 | 2 | | 5:00 |
| 3 | 3b | 2:00 | 2 | | 2:45 |
| mean = 3.3 | | 3:04 | mean = 4.0 | | 4:37 |
| SEM = 0.6 | | 0:37 | SEM = 0.6 | | 0:23 |
| ½ BOLUS score | rxn | time | ½ BOLUS score | rxn | time |
| 5 M | 3a | 5:00 | 5 M | 0 | 5:00 |
| 5 M | 3b | 5:00 | 2 | | 5:00 |
| 3 | 3a | 2:45 | 2 | | 2:00 |
| 3 | 3c | 2:00 | 5 M | 0 | 5:00 |
| 4 | 2b | 4:00 | 2 | | 3:45 |
| 5 M | 0 | 5:00 | 1 | | 2:00 |
| mean = 4.2 | | 3:58 | mean = 2.8 | | 3:47 |
| SEM = 0.4 | | 0:32 | SEM = 0.7 | | 0:36 |
| PERCENT REACTIONS: | | 77.8 | PERCENT REACTIONS: | | 11.1 |

M = needed more drug to complete the euthanasia, did not die within 5:00 minutes.
0 = no reaction, 1 = looked at leg, 2 = pulled leg, 3 = vocalized.
a = slight, b = modertate, c = strong
*Cat also reacted to B/A injection.

For solution #1, the non-premedicated cats scored 3.5 overall with 66.7% showing reactions to the injection. All six cats given 3.5 ECKB IV push reacted to the injection. If given IV over 15 seconds (IV slow), 33 per cent of the cats reacted and 33 percent needed more drug. The ½ bolus technique was even less favorable.

In the group of cats that were premedicated and given 3.5 ECKB, the best score was by IV push with time of death at 3:00±0:32. Only one cat had a slight reaction and the same cat reacted to the premedication. If given more slowly, only one cat reacted but 33 per cent needed more drug to achieve death. Adding lidocaine HCl (ECKL) to the mixture did not help in the non-premedicated cats (Table 9).

TABLE 9
COMPARISON OF ECKB AND ECKL WITHOUT PREMEDICATION IN CATS EUTHANIZED WITH THREE DIFFERENT METHODS OF INJECTION

| Solution #1 3.5 ECKB - no premed | | | Solution #2 3.5 ECKL - no premed | | |
|---|---|---|---|---|---|
| IV PUSH score | rxn | time | IV PUSH score | rxn | time |
| 5 M | 3a | 5:00 | 5 M | 2b | 5:00 |
| 3 | 3c | 1:00 | 5 M | 2b | 5:00 |
| 5 | 3c | 1:30 | 3 | 3c | 1:30 |
| 3 | 3b | 1:30 | 1 A | | 2:30 |
| 3 | 3c | 2:15 | 3 | 3c | 2:00 |
| 3 | 2c | 3:00 | 1 | | 2:30 |
| mean = 3.7 | | 2:22 | mean = 3.0 | | 3:05 |
| SEM = 0.4 | | 0:36 | SEM = 0.7 | | 0:37 |
| IV SLOW score | rxn | time | IV SLOW score | rxn | time |
| 5 M | 0 | 5:00 | 1 | | 3:00 |
| 3 | 3b | 3:00 | 3 | 1a | 1:30 |
| 1 | | 2:00 | 5 M | 2c | 5:00 |
| 3 | 3a | 2:00 | 3 | 2a | 2:30 |
| 5 M | 0 | 5:00 | 5 M | 3c | 5:00 |
| 2 | | 2:45 | 3 | 3b | 2:00 |
| mean = 3.2 | | 3:17 | mean = 3.3 | | 3:04 |
| SEM = 0.7 | | 0:34 | SEM = 0.6 | | 0:37 |
| ½ BOLUS score | rxn | time | ½ BOLUS score | rxn | time |
| 5 M | 1c | 5:00 | 5 M | 3a | 5:00 |
| 3 | 3c | 1:30 | 5 M | 3b | 5:00 |
| 3 | 2b | 2:45 | 3 | 3a | 2:45 |
| 2 | | 4:30 | 3 | 3c | 2:00 |
| 5 M | 3a | 5:00 | 4 | 2b | 4:00 |
| 5 M | 0 | 5:00 | 5 M | 0 | 5:00 |
| mean = 3.8 | | 3:58 | mean = 4.2 | | 3:58 |
| SEM = 0.5 | | 0:36 | SEM = 0.4 | | 0:32 |

Seventy-seven per cent reacted and the mean time of death was not different.

TABLE 10
CATS
COMPARISON OF ECKB AND ECKL WITH BUTORPHANOL/ACEPROMAZINE PREMEDICATION PRIOR TO EUTHANASIA USING THREE DIFFERENT METHODS OF INJECTION

| Solution #1 3.5 ECKB - B/A premed | | | Solution #2 3.5 ECKL - B/A premed | | |
|---|---|---|---|---|---|
| IV PUSH score | rxn | time | IV PUSH score | rxn | time |
| 2 | | 3:00 | 3 | 3c | 3:00 |
| 2 | | 4:55 | 5 M | 0 | 5:00 |
| 3 | 1a* | 1:00 | 2 | | 4:00 |
| 2 | | 4:00 | 2 | | 3:00 |
| 1 | | 2:30 | 5 M | 0 | 5:00 |
| 1 | | 2:45 | 2 | | 4:00 |
| mean = 1.8 | | 3:00 | mean = 3.2 | | 4:00 |
| SEM = 0.3 | | 0:32 | SEM = 0.6 | | 0:22 |
| IV SLOW score | rxn | time | IV SLOW score | rxn | time |
| 5 M | 0 | 5:00 | 5 M | 0 | 5:00 |
| 2 | | 4:00 | 5 M | 2a | 5:00 |
| 5 M | 2a | 5:00 | 5 M | 0 | 5:00 |
| 1 | | 2:00 | 5 M | 0 | 5:00 |
| 2 | | 4:30 | 2 | | 5:00 |
| 2 | | 4:00 | 2 | | 2:45 |
| mean = 2.8 | | 4:05 | mean = 4.0 | | 4:37 |
| SEM = 0.7 | | 0:27 | SEM = 0.6 | | 0:23 |
| ½ BOLUS score | rxn | time | ½ BOLUS score | rxn | time |
| 5 M | 0 | 5:00 | 5 M | 0 | 5:00 |
| 2 | | 5:00 | 2 | | 5:00 |
| 4 | 3b | 5:00 | 2 | | 2:00 |
| 4 | 2b | 5:00 | 5 M | 0 | 5:00 |
| 3 | 3a | 2:00 | 2 | | 3:45 |
| 2 | | 4:45 | 1 | | 2:00 |
| mean = 3.3 | | 4:28 | mean = 2.8 | | 3:47 |
| SEM = 0.5 | | 0:30 | SEM = 0.7 | | 0:36 |

If given slowly, 1 of the 6 cats reacted and the duration was more than 5 minutes in 66 per cent of the cats. It is interesting to note that giving the 3.5 ECKL solution to premedicated cats by ½ bolus eliminated the reactions but 33 per cent of the animals took longer than 5 minutes to die, which is unacceptable. In comparing the premedicated cats euthanized with ECKB or ECKL, the best results was with ECKB using the IV push technique.

DISCUSSION

It is apparent that premedication with 0.1 mg/kg of butorphanol and 0.15 mg/kg of acepromazine eliminated the problem of agonal breathing in both dogs and cats. It also dramatically decreased the incidence of injection reactions in cats. It appears that adding lidocaine HCl was most effective in dogs if they were premedicated. However, the lower embutramide solution, e.g., 3.5 vs 4.0 gm in the stock solution without lidocaine was also effective in dogs. To prevent agonal breathing, premedication with butorphanol and acepromazine may be used and the solution can be given by IV push or slow IV over a 15 second period.

In cats, the 3.5 ECKB solution was most effective in premedicated cats and the time of death was about 3 minutes if they were premedicated. It is also important to note that the premedicated group given 3.5 ECKL had the highest percentage of cats that needed more drug to complete euthanasia, yet the lowest incidence of injection reaction. The fewest cats needing more drug was in the premedicated group for 3.5 ECKB which is the solution with the best score.

In cats, the 3.5 ECKB solution at 0.25 ml/kg yields an approximate dose for each component as follows (Table 11): 44 mg/kg embutramide, 11 mg/kg chloroquine, and 0.6 mg/kg potassium.

TABLE 11
MG/KG DOSAGES
COMPOSITION AND DOSES OF EMBUTRAMIDE, CHLOROQUINE DIPHOSPHATE AND POTASSIUM CHLORIDE WITH AND WITHOUT LIDOCAINE HCl

| | SOLUTION #1 3.5 ECKB | | SOLUTION #2 3.5 ECKL | |
|---|---|---|---|---|
| CHEMICAL ml/kg dose | DOG 0.35 ml/kg | CAT 0.25 ml/kg | DOG 0.35 ml/kg | CAT 0.25 ml/kg |
| embutramide (E) (mg) | 61.2 | 43.7 | 61.2 | 43.7 |
| chloroquine (C) (mg) | 15.3 | 11.0 | 15.3 | 11.0 |
| KCl (mg) | 0.87 | 0.6 | 0.9 | 0.6 |
| NaHCO$_3$ (B) (mg) | 3.3 | 2.4 | XXXX | XXXX |
| lidocaine hydrochloride (mg) | 0 | 0 | 0.7 | 0.5 |

CONCLUSION

The use of B/A premedication in both dogs and cats has the advantage of eliminating undesirable side effects (agonal breathing and injection reactions) and additionally, provides for a calmer more aesthetically pleasing euthanasia. The preferred dose of the compositions tested in this phase were 0.35 ml/kg for dogs and 0.25 ml/kg for cats.

EXAMPLE 2

The 3.5 ECKL solutions were given intraperitoneally to kittens and puppies less than 10 days old and this route was effective as shown in Tables 12 and 13.

TABLE 12

COMPARISON OF THREE DOSES OF ECKL TO ONE DOSE OF ECKL-HCl IN CATS*

| score | rxn | time | score | rxn | time |
|---|---|---|---|---|---|
| 3.5 ECKL 0.25 ml/kg | | | 3.5 ECKL 0.30 ml/kg | | |
| 1 | 0 | 1:45 | 1 | 0 | 2:00 |
| 1 | 0 | :45 | 1 | 0 | 1:00 |
| 1 | 0 | 1:10 | 1 | 0 | 2:30 |
| 1 | 0 | 1:30 | 1 A | 0 | 2:00 |
| 1 | 0 | 2:45 | 1 | 0 | 3:00 |
| mean = 1.0 | | 1:36 | mean = 1.0 | | 2:06 |
| SEM = 0 | | 0:20 | SEM = 0 | | 0:20 |
| 3.5 ECKL 0.35 ml/kg | | | 3.5 ECKL-HCl 0.25 ml/kg | | |
| 1 | 0 | 1:00 | 1 | 0 | 5:00 |
| 1 | 0 | 1:30 | 3 | 3 | 2:00 |
| 1 | 0 | 2:00 | 3 | 3 | 2:15 |
| 1 | 0 | 2:00 | 5 A | 0 | 5:00 |
| 3 | 3 | 2:30 | 5 M | 3 | 5:00 |
| mean = 1.4 | | 1:38 | mean = 3.4 | | 3:12 |
| SEM = 0.4 | | 0:15 | SEM = 0.8 | | 0:44 |

M = needed more drug to complete the euthanasia, did not die within five minutes.
A = Agonal breathing.
*ECKL = Embutramide, chloroquine diphosphate, potassium chloride, lidocaine base.
ECKL-HCl = same as above except L = lidocaine-HCl.

TABLE 13

COMPARISON OF THREE DOSES OF ECKL TO ONE DOSE OF ECKL-HCl IN DOGS*

| score | rxn | time | score | rxn | time |
|---|---|---|---|---|---|
| 3.5 ECKL 0.25 ml/kg | | | 3.5 ECKL 0.30 ml/kg | | |
| 5 M | 0 | 5:00 | 1 A | 0 | 1:30 |
| 5 M | 0 | 5:00 | 2 | 0 | 3:30 |
| 4 | 0 | 4:30 | 5 | 0 | 6:00 |
| 5 M | 0 | 5:00 | 5 | 0 | 5:10 |
| 4 | 0 | 4:30 | 5 | 0 | 6:00 |
| mean = 4.6 | | 4:48 | mean = 3.6 | | 4:26 |
| SEM = 0.3 | | 0:07 | SEM = 0.9 | | 0:52 |
| 3.5 ECKL 0.35 ml/kg | | | 3.5 ECKL-HCl 0.45 ml/kg | | |
| 2 | 1 | 4:00 | 5 M | 1 | 5:00 |
| 1 | 0 | 2:15 | 1 | 0 | :45 |
| 2 | 0 | 3:30 | 1 A | 0 | 1:45 |
| 1 | 0 | 1:30 | 1 A | 0 | 2:45 |
| 1 | 0 | 2:15 | | | |
| mean = 1.4 | | 2:42 | mean = 2.0 | | 2:30 |
| SEM = 0 | | 0:27 | SEM = 1 | | 0:55 |

M = needed more drug to complete the euthanasia, did not die within five minutes.
A = Agonal breathing.
*ECKL = Embutramide, chloroquine diphosphate, potassium chloride, lidocaine base.
ECKL-HCl = same as above except L = lidocaine-HCl.

EXAMPLE 3

This example relates to tests conducted with embutramide, chloroquine, and potassium and substituting lidocaine HCl with lidocaine base. A 3.5 gr embutramide stock solution (3.5 ECKL) was compared with the 4.0 gr embutramide stock solution (4.0 ECKL). Dose response studies were carried out in dogs and cats including 10 animals per dose determination. Methods:

The same format and procedures were used as in Example 1 with catheter placement in animals scheduled for euthanasia at the Ingham County Animal Control Facility in Mason, Mich. The scoring system used is listed in Table 4. The formulas for the ECKL mixtures are listed in Table 14. Three (3) doses of 3.5 ECKL at 0.25, 0.30, and 0.35 ml/kg and 4.0 ECKL at 0.20, 0.25, and 0.30 ml/kg in cats were compared. In addition, 3 doses of 3.5 ECKL at 0.30, 0.35, and 0.40 and 4.0 ECKL at 0.25, 0.30, and 0.35 ml/kg in dogs were compared.

TABLE 14

STOCK SOLUTIONS

| | |
|---|---|
| A. | 3.5 grams embutramide in 10 ml of stock denatured alcohol |
| B. | 4.0 grams embutramide in 10 ml of stock denatured alcohol |
| C. | 2 grams chloroquine diphosphate in 10 ml of $H_2O$ |
| D. | 100 mg KCl in 6.25 ml $H_2O$ + 3.75 ml of 2% lidocaine HCl solution* |
| E. | 100 mg KCl in 6.25 ml, $H_2O$ + 3.75 ml of 2% lidocaine solution* |

MIXTURES
1. A + .5 C + .5 D
2. A + .5 C + .5 E
3. B + .5 C + .5 D
4. B + .5 C + .5 E

*Lidocaine base mixed in 100% denatured alcohol

In addition, 2 horses were euthanized with the 3.5 ECKL solution, one with approximately 0.35 ml/kg (est. 350 lbs) and 0.30 (est. 900 lbs).

RESULTS

The results are listed in Tables 15, 16, 17 and 18. It was concluded from these dose determinations that the most effective dose for dogs was 3.5 ECKL at a dose of 0.35 ml/kg and for cats, the same mixture at a dose of 0.25 ml/kg.

TABLE 15

COMPARISON OF THREE DOSES OF 3.5 EMBUTRAMIDE, CHLOROQUINE DIPHOSPHATE, POTASSIUM CHLORIDE, AND LIDOCAINE BASE (ECKL) UNPREMEDICATED IN CATS

| 3.5 ECKL 0.25 ml/kg | | | 3.5 ECKL 0.30 ml/kg | | |
|---|---|---|---|---|---|
| score | rxn | time | score | rxn | time |
| 1 | 0 | 1:45 | 1 | 0 | 2:00 |
| 1 | 0 | :45 | 1 | 0 | 1:00 |
| 1 | 0 | 1:15 | 1 | 0 | 2:30 |
| 1 | 0 | 1:30 | 1 A | 0 | 2:00 |
| 1 | 0 | 2:45 | 1 | 0 | 3:00 |
| 1 | 0 | 1:30 | 1 | 0 | 2:30 |
| 3 | 1 | 2:00 | 1 | 0 | 2:30 |
| 2 | 0 | 4:30 | 1 | 0 | 2:00 |
| 1 | 0 | 1:30 | 3 A | 3 | 2:30 |
| 5M | 1 | 5:00 | 1 | 0 | 2:00 |
| mean = 1.7 | | 2:25 | 1.2 | | 2:20 |
| SEM = 0.4 | | 0:27 | 0.2 | | 0:10 |

| 3.5 ECKL 0.35 ml/kg | | |
|---|---|---|
| score | rxn | time |
| 1 | 0 | 1:00 |
| 1 | 0 | 1:30 |
| 1 | 0 | 2:00 |
| 1 | 0 | 2:00 |
| 3 | 3 | 2:30 |
| 1 | 0 | 2:00 |
| 1 | 0 | 2:30 |
| 1 | 0 | 1:30 |
| 1 | 0 | 2:00 |
| 4 | 2 | 4:00 |
| mean = 1.5 | | 2:10 |

TABLE 15-continued

COMPARISON OF THREE DOSES OF 3.5 EMBUTRAMIDE, CHLOROQUINE DIPHOSPHATE, POTASSIUM CHLORIDE, AND LIDOCAINE BASE (ECKL) UNPREMEDICATED IN CATS

| SEM = 0.3 | | 0:16 |
|---|---|---|

M = needed more drug to complete the euthanasia, did not die within 5:00 min
A = Agonal breathing

TABLE 16

COMPARISON OF THREE DOSES OF 3.5 EMBUTRAMIDE, CHLOROQUINE DIPHOSPHATE, POTASSIUM CHLORIDE, AND LIDOCAINE BASE (ECKL) IN UNPREMEDICATED DOGS

| 3.5 ECKL 0.30 ml/kg | | |
|---|---|---|
| score | rxn | time |
| 1 A | 0 | 1:30 |
| 2 | 0 | 3:30 |
| 5 | 0 | 6:00 |
| 5 | 0 | 5:10 |
| 5 | 0 | 6:00 |
| 2 | 0 | 4:00 |
| 5 M | 0 | 5:00 |
| 1 | 0 | 2:30 |
| 1 | 0 | 2:30 |
| 2 A | 0 | 3:30 |
| mean = 2.9 | | 5:00 |
| SEM = 0.6 | | 0:30 |

| 3.5 ECKL 0.35 ml/kg | | | 3.5 ECKL 0.45 ml/kg | | |
|---|---|---|---|---|---|
| score | rxn | time | score | rxn | time |
| 2 | 1 | 4:00 | 5 M | 1 | 5:00 |
| 1 | 0 | 2:15 | 1 | 0 | :45 |
| 2 | 0 | 3:30 | 1 A | 0 | 1:45 |
| 1 | 0 | 1:30 | 1 A | 0 | 2:45 |
| 1 | 0 | 2:15 | 5 M | 0 | 5:00 |
| 1 | 0 | 2:40 | 1 | 0 | 2:00 |
| 1 | 0 | 3:00 | 1 A | 0 | 2:30 |
| 2 | 0 | 3:30 | 1 | 0 | 2:00 |
| 1 A | 0 | 2:45 | 1 | 0 | 2:30 |
| 2 | 0 | 3:30 | 5 M | 0 | 5:00 |
| mean = 1.4 | | 3:48 | 2.2 | | 3:55 |
| SEM = 0.2 | | 0:15 | 0.6 | | 0:29 |

M = needed more drug to complete the euthanasia, did not die within 5:00 min
A = agonal breathing

TABLE 17

COMPARISON OF THREE DOSES OF 4.0 EMBUTRAMIDE, CHLOROQUINE DIPHOSPHATE, POTASSIUM CHLORIDE AND LIDOCAINE BASE (ECKL) IN UNPREMEDICATED DOGS

| 4.0 ECKL 0.25 ml/kg | | |
|---|---|---|
| score | rxn | time |
| 2 | 0 | 4:30 |
| 5 M | 0 | 5:00 |
| 1 A | 0 | 3:00 |
| 5 M | 0 | 5:00 |
| 5 | 0 | 8:00 |
| 2 | 0 | 4:00 |
| 4 | 1 | 4:30 |
| 5 M | 0 | 5:00 |
| 1 | 0 | 2:45 |
| 1 | 0 | 2:30 |
| mean = 3.1 | | 4:43 |
| SEM = 0.6 | | 0:30 |

| 4.0 ECKL 0.30 ml/kg | | | 4.0 ECKL 0.35 ml/kg | | |
|---|---|---|---|---|---|
| score | rxn | time | score | rxn | time |
| 5 M | 0 | 4:30 | 2 | 0 | 4:30 |
| 5 M | 0 | 5:00 | 2 | 0 | 3:30 |
| 1 | 0 | 2:30 | 3 | 1 | 1:00 |
| 2 | 0 | 3:15 | 5 M | 0 | 5:00 |
| 1 | 0 | 2:00 | 2 | 0 | 4:45 |
| 2 A | 0 | 3:05 | 1 A | 0 | 2:30 |
| 2 | 0 | 4:30 | 5 M | 0 | 5:00 |
| 5 M | 0 | 5:00 | 1 | 0 | 2:45 |

TABLE 17-continued

COMPARISON OF THREE DOSES OF 4.0 EMBUTRAMIDE, CHLOROQUINE DIPHOSPHATE, POTASSIUM CHLORIDE AND LIDOCAINE BASE (ECKL) IN UNPREMEDICATED DOGS

| 2 | 0 | 3:30 | 1 | 0 | 2:30 |
|---|---|---|---|---|---|
| 1 | 0 | 1:30 | 1 A | 0 | 2:00 |
| mean = 2.6 | | 3:48 | 2.3 | | 3:35 |
| SEM = 0.5 | | 0:24 | 0.5 | | 0:27 |

M = needed more drug to complete the euthanasia, did not die within 5:00 min
A = agonal breathing

TABLE 18

COMPARISON OF THREE DOSES OF 4.0 EMBUTRAMIDE, CHLOROQUINE DIPHOSPHATE, POTASSIUM CHLORIDE AND LIDOCAINE BASE (ECKL) IN UNPREMEDICATED CATS

| 4.0 ECKL 0.20 ml/kg | | |
|---|---|---|
| score | rxn | time |
| 4 | 0 | 4:00 |
| 1 | 0 | 2:00 |
| 5 M | 0 | 5:00 |
| 1 | 0 | 2:30 |
| 5 M | 1 | 5:00 |
| 1 | 0 | 1:00 |
| 2 | 0 | 4:00 |
| 1 | 0 | 2:00 |
| 1 | 0 | 3:00 |
| 1 | 0 | 3:00 |
| 2 | 0 | 4:15 |
| mean = 2.2 | | 3:25 |
| SEM = 0.5 | | 0:24 |

| 4.0 ECKL 0.25 ml/kg | | | 4.0 ECKL 0.30 ml/kg | | |
|---|---|---|---|---|---|
| score | rxn | time | score | rxn | time |
| 1 | 0 | 2:00 | 2 | 0 | 3:20 |
| 1 | 0 | 2:30 | 1 | 0 | 3:00 |
| 2 | 0 | 4:00 | 1 | 0 | 2:30 |
| 1 | 0 | 3:00 | 1 | 0 | 1:30 |
| 1 | 0 | 2:00 | 1 | 0 | 2:00 |
| 1 | 0 | 3:00 | 3 | 2 | 1:45 |
| 1 | 0 | 2:00 | 2 | 0 | 4:00 |
| 5 M | 3 | 5:00 | 4 | 0 | 4:00 |
| 1 | 0 | 2:00 | 1 | 0 | 2:15 |
| 1 | 0 | 3:00 | 1 | 0 | 1:00 |
| 3 | 3 | 2:00 | 2 | 0 | 4:00 |
| mean = 1.6 | | 3:28 | 1.7 | | 3:06 |
| SEM = 0.4 | | 0:18 | 0.3 | | 0:20 |

M = needed more drug to complete the euthanasia, did not die within 5:00 min
A = agonal breathing Euthanasia of the pony and horse went well and were dead within 2 to 3 minutes. Both had minor agonal breaths, 1 and 2 small breaths, respectively, and we suspect that the dose in the horse will be either 0.20 or 0.25 ml/kg IV.

These results show that lidocaine base is more effective in reducing side effects in cats in the preferred compositions.

The results of the testing of the various ingredients in the formulations using procedures of Examples 1 and 3 were as follows:

(1) Two high doses of embutramide (61.6 and 92.4 mg/kg) when used alone were lethal. The three lower doses, 15.5, 23.1, and 31 mg/kg were found to be below the euthanasia threshold. However, from the observations made, it appeared that 31 mg/kg IV might not allow survival. Therefore for safety purposes in survival studies, embutramide was administered at 15.5 and 23.1 mg/kg IV to determine the time of onset of anesthesia and other effects under laboratory conditions in healthy conditioned dogs. There were no significant differences (P$\leq$0.05) between the time of death at the two highest doses (61.6 and 92.4 mg/kg), achieving euthanasia in less than 3 minutes.

(2) With the addition of the cardiotoxins, it was found that the formulation improved when lower amounts of embutramide were used. The amount of embutramide in the final stock solution with embutramide was 3.5 grams and was effective for cats, dogs, and horses. The preferred dose for the animals was as follows: 45 mg/kg for dogs using 0.35 ml/kg of the mixture, 40 mg/kg at 0.30 ml/kg, and 34 mg/kg using 0.25 ml/kg. The preferred effective dose of the euthanasia solution in dogs was 0.35 ml/kg, 0.25 to 0.30 ml/kg for cats, and estimated at 0.25 ml/kg for horses.

(3) The use of butorphanol/acepromazine premedication in both dogs and cats had the advantage of eliminating undesirable side effects (agonal breathing and injection reactions) and additionally, provided for a calmer more aesthetically pleasing euthanasia. The dose tested with premedication was 0.35 ml/kg for dogs and 0.25 ml/kg for cats.

(4) Lidocaine HCl did not solve the problem of injection reactions. Therefore, lidocaine base was substituted for lidocaine HCl as the preferred local anesthetic to reduce injection reactions. With lidocaine base, the most effective dose for dogs was 3.5 ECKL at a dose of 0.35 ml/kg and for cats, the same mixture at a dose of 0.25 ml/kg without adverse side effects. The effective dose for lidocaine is 0.5 to 0.7 mg/kg.

(5) Although the inclusion of this small amount of potassium chloride may not contribute measurably to the effectiveness of the euthanasia solution, it does play a role in improving the formulation and maintaining the stability of the solution. The reason for this phenomenon was and is not clear. The dose of potassium chloride in the formulation ranged from 0.6 to 0.9 mg/kg.

(6) Chloroquine diphosphate was found to be effective in stopping the heart in 3 minutes when combined with embutramide and potassium chloride.

(7) It was evident that increasing the dose with alcohol solutions resulted in an increase in agonal breathing. The alcohol solutions tested were ethanol, isopropyl alcohol and denatured alcohol. The best overall results occurred at the 0.25 and 0.30 ml/kg dose with the ethanol solution and the 0.30 and 0.35 ml/kg with denatured alcohol. These results suggest that denatured alcohol is an alternative solvent for ethanol. Due to high scores and a large number of dogs exhibiting agonal breathing, isopropyl alcohol was not considered for further testing. The preferred solvent used in the formulation was denatured alcohol.

(8) The preferred formulation was comprised of embutramide, chloroquine, lidocaine base, and potassium chloride mixed in denatured alcohol (about 56%) and distilled water (ECKL). To mix the ECKL, 3.5 grams embutramide was added to 10 ml of stock denatured alcohol. The solution was then warmed to be mixed and yielded 13 ml containing 269 mg/ml. Two grams chloroquine diphosphate was added to 10 ml of water and this solution was also warmed for mixing and yielded 11.2 ml containing 178 mg/ml. Potassium chloride (100 mg) was added to 6.25 ml H2O and combined with 75 mg lidocaine dissolved in 3.75 ml denatured alcohol. The potassium chloride concentration was 10 mg/ml and that of lidocaine was 7.5 mg/ml. The stock solutions were:

A. 3.5 grams embutramide added to 10 ml of stock denatured alcohol solution warmed when mixed and yielded 13 ml containing 269 mg/ml.

B. 2 grams chloroquine diphosphate added to 10 ml of water solution warmed when mixed and yielded 11.25 ml containing 178 mg/ml.

C. 100 mg potassium chloride added to 6.25 ml water plus 75 mg lidocaine in 3.75 ml denatured alcohol. The potassium chloride concentration was 10 mg/ml and lidocaine was 7.5 mg/ml.

D. 75 mg lidocaine was dissolved in 3.75 ml of denatured alcohol plus 6.25 ml distilled water. The lidocaine was 7.5 mg/ml. The mixtures tested were:

1. A +.5 B +.5 C and
2 A +.5 B +.5 D reflecting the use of either the lidocaine base or lidocaine hydrochloride. The amounts are by volume. Solution comprised of about 56% denatured alcohol.

The doses of the compounds used in the formulations were as shown in Table 19.

TABLE 19

COMPOSITION AND DOSES OF ECKL

| COMPONENT | CONCENTRATION: MG/ML | DOSE:MG/KG |
|---|---|---|
| Embutramide | 135 | 0.25 ml/kg = 34 |
| | | 0.30 ml/kg = 40 |
| | | 0.35 ml/kg = 45 |
| Chloroquine diphosphate | 45 | 0.25 ml/kg = 11 |
| | | 0.30 ml/kg = 14 |
| | | 0.35 ml/kg = 16 |
| Lidocaine Base | 1.9 | 0.25 ml/kg = 0.5 |
| | | 0.30 ml/kg = 0.6 |
| | | 0.35 ml/kg = 0.7 |
| KCl | 2.5 | 0.25 ml/kg = 0.60 |
| | | 0.30 ml/kg = 0.75 |
| | | 0.35 ml/kg = 0.90 |

The solvent was denatured alcohol, 95 parts by volume, ethyl alcohol and 5 parts methyl alcohol.

It is intended that the foregoing description be only illustrative of the present invention and that the present invention be limited only by the hereinafter appended claims.

We claim:

1. A method for providing euthanasia in a mammal in need thereof which comprises:
   (a) premedicating by intravenous administration to tranquilize the mammal with a tranquilizer immediately prior to euthanasia; and
   (b) introducing by injection into the mammal an aqueous euthanasia solution comprising an effective amount for producing euthanasia of a cardiotoxic compound selected from the group consisting of a quinacrine compound and a chloroquine compound and a water solubilized gamma-hydroxybutramide in an anesthetic amount, wherein euthanasia occurs in the mammal.

2. The method of claim 1 wherein the tranquilizer is acepromazine.

3. The method of claim 1 wherein the tranquilizer includes an analgesic.

4. The method of claim 3 wherein the analgesic is butorphanol.

5. A method for providing euthanasia in a mammal in need thereof which comprises introducing by injection into the mammal an aqueous solution comprising in admixture an effective amount for producing euthanasia of a cardiotoxic compound selected from the group consisting of a quinacrine compound and a chloroquine compound, a lidocaine selected from the group consisting of a water-solubilized lidocaine as a base and water soluble salts thereof in a cardiotoxic amount, and a water solubilized gamma-hydroxybutramide in an anesthetic amount, wherein euthanasia occurs in the mammal.

6. The method of claim 5 wherein the chloroquine salt is chloroquine diphosphate or chloroquine base and the quinacrine compound is quinacrine hydrochloride or quinacrine base.

7. A method for providing euthanasia in a mammal in need thereof which comprises:

introducing by injection into the mammal an effective amount for producing euthanasia of a mixture of gamma-hydroxybutramide dissolved in a water miscible liquid solubilizing agent;
a chloroquine compound;
a lidocaine compound; and optionally
a water soluble inorganic salt in an aqueous solution so that the mammal is euthanatized within five (5) minutes.

8. The method of claim 7 wherein the chloroquine compound is chloroquine diphosphate or chloroquine base.

9. The method of claim 7 wherein the liquid solubilizing agent is a lower alkanol containing 1 to 3 carbon atoms.

10. The method of claim 7 wherein the water soluble inorganic salt is potassium chloride.

11. The method of claim 7 wherein the mixture is formulated in a single unit dosage form.

12. The method of claim 7 wherein sodium bicarbonate as a buffer is provided in the solution and the pH of the solution is between about pH 4.5 and 7.2.

13. The method of claim 7 wherein the liquid solubilizing agent is ethanol or denatured ethanol, the chloroquine compound is chloroquine diphosphate or chloroquine base, and the inorganic salt is selected from the group consisting of potassium chloride and sodium chloride.

14. The method of claim 13 wherein the solution contains a ratio of gamma-hydroxybutramide to chloroquine of between 3 to 1 and 6 to 1; gamma-hydroxybutramide to potassium salt of between about 0.01 to 0.02 to 1 and a ratio of lidocaine to gamma-hydroxybutramide of between about 0.01 and 0.015 to 1.

15. The method of claim 14 wherein the solution is introduced into the blood stream of the mammal at a dosage between about 0.15 and 0.35 ml per kg of body weight of the mammal.

16. The method of claim 7 wherein the solution is in an injectable form and contains between about 35 and 75 mg of gamma-hydroxybutramide; between about 5 and 20 mg of chloroquine compound, between about 0.2 and 1 mg of the lidocaine compound and between about 0.5 to 3 mg of inorganic salt per kg of body weight of the mammal which is administered to the mammal in the solution as a single dosage unit.

17. The method of claim 7 wherein the mammal is a domesticated animal.

18. The method of claim 7 wherein the mammal is a cat.

19. The method of claim 5 wherein the mammal is premedicated by intravenous administration to tranquilize the mammal with an analgesic and a tranquilizer immediately prior to injecting the solution to reduce agonal breathing during euthanasia.

20. The method of claim 19 wherein the tranquilizer is acepromazine and the analgesic is butorphanol.

21. A composition for providing euthanasia in a mammal which comprises in admixture in an injectable aqueous solution:

(a) a cardiotoxic compound selected from the group consisting of a quinacrine compound and a chloroquine compound;
(b) a lidocaine selected from the group consisting of a water solubilized lidocaine as a base and water soluble salts thereof;
(c) gamma-hydroxybutramide, wherein the solution contains a ratio of gamma-hydroxybutramide to chloroquine or quinacrine of between about 3 to 1 and 6 to 1 and a ratio of lidocaine to gamma-hydroxybutramide of between about 0.01 and 0.15 to 1 in an amount sufficient to produce euthanasia; and
(d) an injectable carrier.

22. The composition of claim 19 wherein the chloroquine compound is chloroquine diphosphate and the quinacrine is quinacrine hydrochloride or chloroquine base or quinacrine base.

23. The composition of claim 22 in a multiple dosage form.

24. The composition of claim 23 wherein the dosage form provides between about 0.15 and 0.35 ml per kg of body weight of each mammal to produce death.

25. A composition for providing euthanasia in a mammal which comprises in admixture an aqueous solution:

(a) gamma-hydroxybutramide dissolved in a water immiscible liquid solubilizing agent;
(b) a water soluble chloroquine compound;
(c) a lidocaine compound; and
(d) a water soluble potassium salt, wherein the solution contains a ratio of gamma-hydroxybutramide to chloroquine salt of between about 3 to 1 and 6 to 1; a ratio of gamma-hydroxybutramide to potassium salt of between about 0.01 and 0.02 and a ratio of lidocaine compound to gamma-hydroxybutramide between about 0.01 and 0.015 to 1 and wherein the solution produces euthanasia; and
(e) an injectable carrier.

26. The composition of claim 25 in a single unit dosage form containing between about 0.15 and 0.35 ml per kg of body weight of the mammal.

27. The composition of claim 25 wherein the aqueous solubilizing agent is selected from the group consisting of ethanol and denatured ethanol, the chloroquine compound is chloroquine diphosphate or chloroquine base and the inorganic salt is selected from the group consisting of potassium chloride and sodium chloride.

28. The composition of claim 27 wherein sodium bicarbonate is provided in the solution as a buffer and the pH of the solution is between about pH 4.5 and 7.2.

29. The composition of claim 27 in a single unit dosage form.

* * * * *

UNITED STATES PATENT AND TRADEMARK OFFICE
CERTIFICATE OF CORRECTION

PATENT NO. : 5,290,775
DATED : March 1, 1994
INVENTOR(S) : Donald C. Sawyer, Marlee A. Langham and Theodore M. Brody It is certified that error appears in the above—identified patent and that said Letters Patent is hereby corrected as shown below:

Title page, Column 2, lines 3 and 4, "Formula Y" should read --Formulary--.

Column 5, line 30, a -- + -- sign should be inserted after --water--.

Column 5, line 34, a -- + -- sign should be inserted after --powder--.

Column 6, line 68, "amount" should read --amounts--.

Column 7, line 27, "does" should read --dose--.

Column 7, line 43, "does" should read --dose--.

Column 15, line 27, "5:00" should read --1:45--.

Column 19, line 61, "H2O" should read --$H_2O$--.

Signed and Sealed this

Thirtieth Day of August, 1994

*Attest:*

BRUCE LEHMAN

*Attesting Officer*  *Commissioner of Patents and Trademarks*